(12) United States Patent
Tanaka et al.

(10) Patent No.: US 7,993,668 B2
(45) Date of Patent: Aug. 9, 2011

(54) NUTRIENT COMPOSITION AND COMPOSITION FOR PREVENTION/MITIGATION OF DIGESTIVE TRACT DEPRESSION

(75) Inventors: Tatsuro Tanaka, Kawasaki (JP); Hisayuki Uneyama, Kawasaki (JP); Kunio Torii, Kawasaki (JP); Kiyoshi Miwa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1203 days.

(21) Appl. No.: 11/617,137

(22) Filed: Dec. 28, 2006

(65) Prior Publication Data

US 2007/0218109 A1 Sep. 20, 2007

Related U.S. Application Data

(63) Continuation of application No. PCT/JP2005/012010, filed on Jun. 23, 2005.

(30) Foreign Application Priority Data

Jun. 28, 2004 (JP) ................................. 2004-189515

(51) Int. Cl.
*A61K 47/00* (2006.01)

(52) U.S. Cl. ........................................................ 424/439

(58) Field of Classification Search ........................ None
See application file for complete search history.

(56) References Cited

U.S. PATENT DOCUMENTS

| | | | | |
|---|---|---|---|---|
| 3,156,569 A | * | 11/1964 | Griffin et al. | 426/536 |
| 3,821,471 A | * | 6/1974 | Bauer | 381/22 |
| 3,832,471 A | * | 8/1974 | Siregar | 426/2 |
| 4,176,201 A | * | 11/1979 | Cook | 426/548 |

FOREIGN PATENT DOCUMENTS

| | | | |
|---|---|---|---|
| JP | 06303918 A | * | 11/1994 |
| JP | 7-330583 | | 12/1995 |
| JP | 2003-524636 | | 8/2003 |
| JP | 2003-530411 | | 10/2003 |
| JP | 2004313178 A | * | 11/2004 |
| WO | 98/32429 | | 7/1998 |
| WO | 01/45691 | | 6/2001 |
| WO | 01/78532 | | 10/2001 |
| WO | 02/062324 | | 8/2002 |

OTHER PUBLICATIONS

Glutamic Acid. WWW.nutros.com/nsr-0200d.html.*
WebMD article, Causes of Diarrhea, accessed May 31, 2010.*

(Continued)

*Primary Examiner* — Anand Desai
*Assistant Examiner* — Melissa S Mercier
(74) *Attorney, Agent, or Firm* — Oblon, Spivak, McClelland, Maier & Neustadt, L.L.P.

(57) ABSTRACT

As a nutritional composition and a composition for the prophylaxis or improvement of lower gastrointestinal function, which improve lower gastrointestinal function and are effective for the prophylaxis or improvement of diarrhea, gastroesophageal reflux or misswallowing caused by administration of a liquid nutritional supplement, the present invention provides a nutritional composition and a composition for the prophylaxis or improvement of lower gastrointestinal function, which comprise at least one kind selected from glutamic acid, 5'-nucleotide and a salt thereof, wherein, when glutamic acid alone is contained, the content thereof on administration is 0.0013-1.3 w/v % as free glutamic acid.

17 Claims, 2 Drawing Sheets

OTHER PUBLICATIONS

L. S. Vasilevskaia, et al. "Effect of glutamate and combined with inosine monophosphate on gastric secretion" Database Medline, US National Library of Medicine, May 1993, XP-002445428, p. 1-1.

Jean-Pierre Kessler, et al. "Evidence that activation of N-methyl-D-aspartate (NMDA) and non-NMDA receptors within the nucleus tractus solitarii triggers swallowing" European Journal of Pharmacology, vol. 201, 1991, XP-002447629, pp. 59-67.

Pamela J Hornby, "Receptors and Transmission in the Brain-Gut Axis II. Excitatory amino acid receptors in the brain-gut axis" American Journal of Physiology: Gastrointestinal and Liver Physiology, American Physiological Society, US, vol. 280, No. 6, 2001, XP-002999857, pp. G1055-G1060.

R. Norton et al, "Use of nucleotides in weanling rats with diarrhea induced by a lactose overload: effect on the evolution of diarrhea and weight and on the histopathology of intestine, liver and spleen", *Brazilian Journal of Medical and Biological Research*, 2001, vol. 34, No. 2, pp. 195-202.

M. Ando, "Amino acid metabolism and water transport across the seawater eel intestine", *Journal of Experimental Biology*, 1988, vol. 138, pp. 93-106.

M. Ando, "Regulation by intracellular alanine of water transport across the seawater eel intestine", *Zoological Science*, 1987, vol. 4, No. 1, pp. 37-44.

U.S. Appl. No. 11/687,805, filed Mar. 19, 2007, Uneyama, et al.

S. Iijima et al., *The Journal of Nutrition*, 126: pp. 589-595 (1996).

Arnaud et al., Journal of Pediatric Gastroenterology and Nutrition, vol. 37 No. 2 (2003) pp. 124-131.

European Search Report issued Feb. 2, 2011 in Application EP 10011493.3.

* cited by examiner

US 7,993,668 B2

NUTRIENT COMPOSITION AND COMPOSITION FOR PREVENTION/MITIGATION OF DIGESTIVE TRACT DEPRESSION

CROSS REFERENCES TO RELATED APPLICATIONS

This application is a continuation of International Patent Application No. PCT/JP05/12010, filed on Jun. 23, 2005, and claims priority to Japanese Patent Application No. 2004-189515, filed on Jun. 28, 2004.

TECHNICAL FIELD

The present invention relates to a nutritional composition and a composition for the prophylaxis or improvement of lower gastrointestinal function, which improve gastrointestinal function, and decrease the frequency of incidents of diarrhea or gastroesophageal reflux or misswallowing developed on administration of a liquid nutritional supplement and the like.

BACKGROUND ART

Patients who had a major operation and the elderly having lower digestive capacity cannot digest food to an absorbable state, and therefore, cannot take sufficient nutrition. It reduces resistance to illness and a recuperative power. Liquid nutritional supplements are used for the maintenance or management of nutrition in such patients, and particularly used for tube feeding of nutrition when oral dietary intake is difficult. Liquid nutritional supplements administered using a tube are called enteral nutrients, which are administered to the stomach, duodenum or jejunum from a nasal tube, gastric fistula or intestinal fistula. According to the symptom, oral intake may be employed for patients capable of oral ingestion.

Liquid nutritional supplements, enteral nutrients among others, are essential for the nutritional maintenance of postoperational patients. Enteral nutrients contain digested nutrients and elemental nutrients and are supplied in the form of a liquid. The incidence of diarrhea, gastroesophageal reflux and misswallowing as side effects of the intake of enteral nutrients is high, which poses problems for the QOL of patients themselves and clinical workers. Needless to say, the onset of diarrhea and the like is also observed as side effects of oral administration of the nutrients.

It is considered that diarrhea, a side effect of liquid nutritional supplements, is caused by lower gastrointestinal physiological function due to fasting before and after operation or operative stress, as well as long-term non-intake of nutrition from the gastrointestinal tract due to postoperative central venous nutrition and the like, and lower gastrointestinal physiological function due to fasting before and after operation. It is also observed in patients with markedly degraded digestive and absorptive capacity due to aging, such as the elderly and the like, and babies and infants having immature digestive and absorptive capacity.

Another major problem of liquid nutritional supplements is gastroesophageal reflux. Patients in the dorsal position during intragastric administration of liquid nutritional supplements by tube feeding or from a gastric fistula may develop aspiration pneumonia because of invasion of gastric contents, which refluxed into the esophagus, to the trachea or lung. Since aspiration pneumonia may sometimes be fatal to a sick person, it is also an extreme threat to the medical workers responsible for protecting patients' lives. Thus, prophylaxis and prevention of gastroesophageal reflux causing misswallowing has been desired.

No effective measures to deal with these side effects caused by the administration of liquid nutritional supplements have been found heretofore, and change, reduction or discontinuation of liquid nutritional supplements, or administration of a therapeutic drug suitable for the symptom and the like have been employed.

As for diarrhea induced by lactose, a report has documented that administration of five kinds of nucleic acids of adenylic acid, guanylic acid, uridylic acid, cytidylic acid and inosinic acid, which are nucleic acids forming RNA, in admixture with a standard diet suppresses diarrhea (R. Norton et al, "Brazilian Journal of Medical and Biological Research", 2001, vol. 34, P. 195-202). However, this report merely suggests a possibility that simultaneous administration of five kinds of nucleic acids may act on the recovery from gastrointestinal mucosa inflammation, for suppression of diarrhea symptoms caused by a particular component of lactose, and no suggestion of effect is provided when one kind thereof is lacking, i.e., when RNA is not formed. In addition, the report contains no description relating to nutritional compositions or liquid nutritional supplements.

As enteral nutrients containing glutamic acid, a liquid preparation containing 24-147 mM (0.36-2.1 w/v %) of free glutamic acid, which is efficiently absorbed and effective as an energy source (JP-A-7-330583), and a composition for the treatment of gastric and intestinal dysfunction, which contains 9.0-17 wt % (in total amino acid composition) of free amino acid including glutamic acid (JP-A-2003-530411), are known. However, used for the both is free glutamic acid, and a glutamic acid salt is not suggested at all. In addition, these publications show enteral nutrients containing glutamic acid as an energy source and nutrient source, and suppression of side effects such as diarrhea and the like, which are developed by enteric nutrient administration of glutamic acid, is not suggested.

DISCLOSURE OF THE INVENTION

The problems to be solved by the present invention is provision of a nutritional composition and a composition for the prophylaxis or improvement of lower gastrointestinal function, which improve lower gastrointestinal function and are effective for the prophylaxis or improvement of diarrhea, gastroesophageal reflux or misswallowing caused by administration of a liquid nutritional supplement.

The present inventors have conducted intensive studies in an attempt to solve the above-mentioned problems and completed the present invention. The present invention encompasses the following.

(1) A nutritional composition comprising at least one kind selected from glutamic acid, 5'-nucleotide and a salt thereof, wherein, when glutamic acid alone is contained, the content thereof on administration is 0.0013-1.3 w/v % as free glutamic acid.

(2) The nutritional composition of (1), which is liquid when in use.

(3) The nutritional composition of (1) or (2), wherein the aforementioned 5'-nucleotide is adenylic acid, inosinic acid, guanylic acid, cytidylic acid, uridylic acid and/or xanthylic acid.

(4) The nutritional composition of any one of (1) to (3), which does not comprise adenylic acid, inosinic acid, guanylic acid, cytidylic acid and uridylic acid at the same time.

(5) The nutritional composition of any one of (1) to (4), wherein the total content of adenylic acid, inosinic acid, guanylic acid, cytidylic acid, uridylic acid, xanthylic acid and a salt thereof is 0.0035-0.41 w/v % as a free acid.
(6) The nutritional composition of any one of (1) to (5), which is used for the prophylaxis and/or improvement of lower gastrointestinal function.
(7) The nutritional composition of any one of (1) to (6), which is used for suppressing the onset of diarrhea and/or gastroesophageal reflux.
(8) The nutritional composition of any one of (1) to (7), which is administered from a gastric fistula or intestinal fistula.
(9) A composition for the prophylaxis or improvement of lower gastrointestinal function, which comprises at least one kind selected from glutamic acid, 5'-nucleotide and a salt thereof, wherein, when glutamic acid alone is contained, the content thereof on administration is 0.0013-1.3 w/v % as free glutamic acid.
(10) The composition of (9), which is liquid when in use.
(11) The composition of (9) or (10), wherein the aforementioned 5'-nucleotide is adenylic acid, inosinic acid, guanylic acid, cytidylic acid, uridylic acid and/or xanthylic acid.
(12) The composition of any one of (9) to (11), which does not comprise inosinic acid, adenylic acid, guanylic acid, cytidylic acid and uridylic acid at the same time.
(13) The composition of any one of (9) to (12), wherein the total content of adenylic acid, inosinic acid, guanylic acid, cytidylic acid, uridylic acid, xanthylic acid and a salt thereof is 0.0035-0.41 w/v % as free acid.
(14) The composition of any one of (9) to (13), which is used for the prophylaxis or improvement of lower gastrointestinal function.
(15) The composition of any one of (9) to (14), which is used for suppressing the onset of diarrhea and/or gastroesophageal reflux.
(16) The composition of any one of (9) to (15), which is administered prior to the administration of a liquid nutritional supplement.
(17) The composition of any one of (9) to (16), which is administered from a gastric fistula or intestinal fistula.
(18) A method for the prophylaxis or improvement of lower gastrointestinal function, which comprises administering an effective amount of a composition comprising at least one kind selected from glutamic acid, 5'-nucleotide and a salt thereof, wherein, when glutamic acid alone is contained, the content thereof on administration is 0.0013-1.3 w/v % as free glutamic acid.
(19) The method of (18), which comprises administration as a liquid.
(20) The method of (18) or (19), wherein the aforementioned 5'-nucleotide is adenylic acid, inosinic acid, guanylic acid, cytidylic acid, uridylic acid and/or xanthylic acid.
(21) The method of any one of (18) to (20), wherein the aforementioned composition does not comprise inosinic acid, adenylic acid, guanylic acid, cytidylic acid and uridylic acid at the same time.
(22) The method of any one of (18) to (21), wherein the total content of adenylic acid, inosinic acid, guanylic acid, cytidylic acid, uridylic acid, xanthylic acid and a salt thereof contained in the aforementioned composition is 0.0035-0.41 w/v % as free acid.
(23) The method of any one of (18) to (22), which is used for the prophylaxis and/or improvement of lower gastrointestinal function.
(24) The method of any one of (18) to (23), which suppresses the onset of diarrhea and/or gastroesophageal reflux.
(25) The method of any one of (18) to (24), which comprises administered prior to the administration of a liquid nutritional supplement.
(26) The method of any one of (18) to (25), which comprises administered from a gastric fistula or intestinal fistula.
(27) Use of glutamic acid, 5'-nucleotide or a salt thereof for the production of a composition for the prophylaxis or improvement of lower gastrointestinal function, which comprises at least one kind selected from glutamic acid, 5'-nucleotide and a salt thereof, wherein, when glutamic acid alone is contained, the content thereof on administration is 0.0013-1.3 w/v % as free glutamic acid.
(28) The use of (27), wherein the aforementioned 5'-nucleotide is adenylic acid, inosinic acid, guanylic acid, cytidylic acid, uridylic acid and/or xanthylic acid.
(29) The use of (27) or (28), wherein the aforementioned composition does not comprise inosinic acid, adenylic acid, guanylic acid, cytidylic acid and uridylic acid at the same time.
(30) The use of any one of (27) to (29), wherein the total content of adenylic acid, inosinic acid, guanylic acid, cytidylic acid, uridylic acid, xanthylic acid and a salt thereof contained in the aforementioned composition is 0.0035-0.41 w/v % as free acid.
(31) The use of any one of (27) to (30), wherein the aforementioned composition is used for the prophylaxis and/or improvement of lower gastrointestinal function.
(32) The use of any one of (27) to (31), wherein the aforementioned composition is used for suppressing the onset of diarrhea and/or gastroesophageal reflux.
(33) The use of any one of (27) to (32), wherein the aforementioned composition is administered prior to the administration of a liquid nutritional supplement.
(34) The use of any one of (27) to (33), wherein the aforementioned composition is administered from a gastric fistula or intestinal fistula.
(35) A commercial package comprising a composition comprising at least one kind selected from glutamic acid, 5'-nucleotide and a salt thereof, wherein, when glutamic acid alone is contained, the content thereof on administration is 0.0013-1.3 w/v % as free glutamic acid and a written matter containing an explanation on the use of the composition for the prophylaxis or improvement of lower gastrointestinal function.

BEST MODE FOR EMBODYING THE INVENTION

Figure 1:
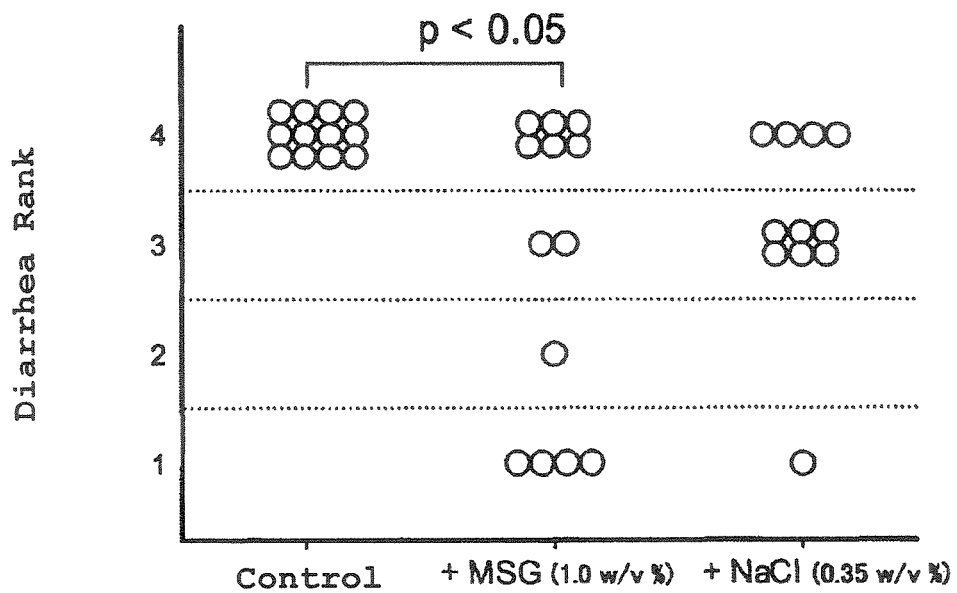
FIG. 1 shows the results of Example 1.

The nutritional composition of the present invention is used to improve lower gastrointestinal function, decrease the frequency of diarrhea as a side effect associated with the administration of liquid nutritional supplement, and prevent or improve gastroesophageal reflux. Since the nutritional composition of the present invention can be administered during the period before and after operation, when enteral feeding is not possible, it can maintain the gastrointestinal function.

The nutritional composition of the present invention is a nutritional composition containing digested nutrients and elemental nutrients, and is generally used for nutritional maintenance in patients who had a major operation, the elderly with lower digestive capacity and the like.

In the present invention, of glutamic acid, adenylic acid, inosinic acid, guanylic acid, cytidylic acid, uridylic acid, xanthylic acid and a salt thereof, glutamic acid, inosinic acid, guanylic acid, xanthylic acid and a salt thereof are what is called umami substances.

Umami is one of the five basic tastes together with salty taste, sweet taste, sour taste and bitter taste and has a peculiar gustation. Addition thereof controls flavor and taste of food. Examples of natural umami substances include glutamic acid which is an amino acid group umami substance, and salts of inosinic acid, guanylic acid and the like, which are nucleic acid group umami substances. While umami substances originally control taste of food and increase the flavor as flavor enhancers, by addition to a nutritional composition, they can remarkably reduce diarrhea, a side effect, and can rapidly activate the lower gastrointestinal physiological function.

An "umami substance" means a substance that provides "umami" that can be clearly distinguished from the aforementioned four basic tastes of sweet taste, salty taste, sour taste and bitter taste. Historically, it began from the use of the term "umami" to express the taste of glutamic acid, which is a peculiar taste that does not fall under sweet, salty, sour and bitter, when Prof. IKEDA Kikunae of the University of Tokyo found glutamic acid from a soup of kelp in 1908. At present, "umami" is recognized as an independent taste element that cannot be created by combining the four basic tastes of sweet taste, salty taste, sour taste and bitter taste, and "umami" is recognized as an international term.

The umami substance includes amino acid group umami substances and nucleic acid group umami substances. The amino acid group umami substance includes various salts such as glutamic acid salt (e.g., sodium glutamate (monosodium glutamate, MSG), potassium glutamate), tricholomic acid salt, ibotenic acid salt, βhydroxy-L-glutamic acid salt, L-homocysteic acid salt, L-aspartic acid salt and the like. On the other hand, the nucleic acid group umami substance includes salts such as sodium 5'-inosinate, sodium 5'-guanylate, sodium 5'-xanthylate, sodium 5'-adenylate, sodium deoxy 5'-adenylate, sodium 2-methylthio-5'-inosinate, sodium N'-methyl-2-methylthio-5'-inosinate and the like.

A nucleic acid is a substance made of pentose, phosphoric acid and a base, and includes adenylic acid, guanylic acid, inosinic acid, cytidylic acid, uridylic acid and xanthylic acid and the like. Of these, adenylic acid, guanylic acid, inosinic acid and xanthylic acid are known nucleic acid group umami substances as mentioned above. Different from umami substances, cytidylic acid and uridylic acid are assumed to have an action to suppress diarrhea caused by liquid nutritional supplements.

The nutritional composition of the present invention contains at least one kind selected from glutamic acid, 5'-nucleotide and a salt thereof. 5'-Nucleotide preferably includes adenylic acid, inosinic acid, guanylic acid, cytidylic acid, uridylic acid and xanthylic acid (provided that adenylic acid, inosinic acid, guanylic acid, cytidylic acid and uridylic acid are not preferably contained at the same time). More preferably, the nutritional composition of the present invention contains at least one kind from the salts of glutamic acid, adenylic acid, inosinic acid, guanylic acid, cytidylic acid, uridylic acid and xanthylic acid. As the salt thereof, sodium salt is particularly preferable. However, when glutamic acid alone is contained, its content is 0.0013-1.3 w/v %, preferably 0.44-0.88 w/v %, as a concentration of free glutamic acid on administration.

In the present invention, only one kind of the component may be used, or two or more kinds thereof may be used in combination. For combination of two or more kinds, 1 to 5 kinds from glutamic acid, a salt thereof and nucleic acid group components and a salt thereof is/are combined, or 2 to 5 kinds from nucleic acid and a salt thereof are combined (however, adenylic acid, inosinic acid, guanylic acid, cytidylic acid and uridylic acid are preferably not contained at the same time).

The nutrient sources to be contained in the nutritional composition of the present invention besides glutamic acid, adenylic acid, inosinic acid, guanylic acid, cytidylic acid, uridylic acid, xanthylic acid and salts thereof are not limited at all, and those conventionally used such as various amino acids, peptides, proteins, carbohydrates, vitamins, lipids, minerals and the like can be used. As the components other than the nutrient sources, known compositions can be used.

The nutritional composition of the present invention is generally used in the form of a liquid (particularly enteral nutrient) for the nutrition maintenance or management in postoperative patients, the elderly, who have lower digestive capacity, and the like. The nutritional composition of the present invention is a liquid or can be prepared into a liquid when in use, and generally used for tube feeding of nutrition when oral dietary intake is difficult for a sick person. The kind of enteral nutrient includes one containing an undigested protein as a main component, one containing a semidigested protein obtained by hydrolysis of protein as a main component, and one containing digested nutrients and elemental nutrients. They are appropriately used according to the pathology and the level of digestive or absorptive dysfunction of a sick person.

The nutritional composition of the present invention is used for the nutritional management before and after operation, diseases requesting cleansing of the inside of the bowel, pathology of gastrointestinal abnormality (ruptured suture, short-bowel syndrome, various gastrointestinal fistulae and the like), special gastrointestinal diseases (Crohn's disease, ulcerative colitis, ischochymia syndrome, pancreatic diseases, protein-losing gastroenteropathy and the like), nutritional management when application of high-calorie transfusion is difficult (extensive burn and the like), the elderly with lower digestive capacity, babies and infants with immature digestive and absorptive capacity and the like.

In addition, the nutritional composition of the present invention is also used for a patient with gastric fistula or intestinal fistula, who is free of gastrointestinal dysfunction. For example, patients for whom oral intake is difficult, such as patients with a disease other than gestrointestinal diseases, such as cerebrovascular disorder, cerebral infarction, Parkinson's syndrome, dementia and the like, are under liquid nutritional supplement administration via a gastric fistula or intestinal fistula, and use for such patients is also encompassed in the present invention.

The dosage form of the nutritional composition of the present invention is not particularly limited and the composition can be administered in the form of a solid, a powder, a liquid, a jelly and the like. Administration of a liquid when in use is preferable. As the administration means, any of the enteral administration, gastric administration and oral administration can be used. In the case of enteral administration or gastric administration, a nasal tube, a gastric fistula or an intestinal fistula is used for administration into the stomach, duodenum or jejunum. According to the symptom, oral intake may be employed for patients capable of oral digestion. Enteral intake or oral intake is appropriately employed depending on the recovery level of digestive and absorptive function after operation or from the pathology. Moreover, the nutritional composition of the present invention can be administered to patients not only as a liquid nutritional supplement for nutritional management, but also as a water supply to patients after addition to the supplementary water. In this case, a form showing viscosity, such as jelly and the like, can also be used.

The nutritional composition of the present invention in the form of a liquid can be administered, for example, by enteric administration, gastric administration or oral administration to an adult in an amount of 400-3000 mL, desirably 800-1200 mL, per day. As regards the dose of glutamic acid, the liquid preparation to be given to a patient preferably contains 0.0013-1.3 w/v % (0.09 mM-90 mM in molar concentration) of sodium glutamate as a free glutamic acid, irrespective of the administration route. When the content is less than 0.0013 w/v %, no effect is provided and when it is higher than 1.3 w/v %, the taste is impaired unpreferably. More preferably, the content is 0.44-0.88 w/v % (30 mM-60 mM). Similarly, nucleic acid is desirably contained in 0.0035-0.41 w/v % (0.1-10 mM) as a free acid. When the content is less than 0.0035 w/v %, no effect is provided and when it is higher than 0.41 w/v %, the taste is impaired unpreferably. More preferably, it is desirably contained in 0.035-0.35 w/v % (1-10 mM). When sodium glutamate and sodium nucleate are mixed, the mixing ratio is desirably 1:0-0.1, at which the taste is not impaired.

The production method of the nutritional composition of the present invention is not particularly limited, and the composition can be produced by a known method. For example, the composition can be provided by a method comprising previously adding at least one kind selected from glutamic acid, adenylic acid, inosinic acid, guanylic acid, cytidylic acid, uridylic acid, xanthylic acid and a salt thereof to a powder or liquid enteral nutrient, or provided as a powder preparation or a liquid preparation used for addition to an existing enteral nutrient when in use. In addition, the nutritional composition of the present invention can suppress gastrointestinal dysfunction such as diarrhea and the like, which is developed by usual enteral nutrient administration, by administration prior to the usual enteral nutrient administration. The formulation in this case consists of the predetermined components of the present invention, and the minimum necessary components for an enteral liquid preparation. When used as a nutritional composition to be separately administered, the components other than glutamic acid, adenylic acid, inosinic acid, guanylic acid, cytidylic acid, uridylic acid, xanthylic acid and a salt thereof are not particularly limited, and carbohydrate, amino acid, vitamin, mineral and the like are used.

The composition for the prophylaxis or improvement of lower gastrointestinal function of the present invention has an effect of preventing and/or improving a lower gastrointestinal function, particularly the onset of diarrhea caused by the administration of liquid nutritional supplements. The composition can also be prepared in the form of a pharmaceutical agent or food. It can be prepared in a form known per se, such as tablet, capsule, powder, liquid, powdered drug and the like, which can contain components known per se necessary for providing these forms. The amount of intake of glutamic acid, adenylic acid, inosinic acid, guanylic acid, cytidylic acid, uridylic acid, xanthylic acid and a salt thereof in the composition is similar to those mentioned above.

The composition may be administered alone or, for example, in combination with an enteral nutrient and the like. For administration in combination with a nutritional supplement, the administration route and the dosage form may be the same or different, and the timing of administration may also be the same or different. They are appropriately determined according to the kind and effect of the nutritional supplements to be used in combination. Particularly, to improve diarrhea, gastroesophageal reflux, misswallowing and lower gastrointestinal function caused by an enteral nutrient to be separately administered, it is generally preferable to administer the composition several days or immediately before administration of the enteral nutrient.

The subject of administration of the composition of the present invention is not particularly limited, and the composition is useful for the prophylaxis or improvement of lower gastrointestinal function in various mammals including human, monkey, mouse, rat, guinea pig, rabbit, swine, dog, horse, bovine etc., and the like.

With regard to the package containing the composition of the present invention and a written matter containing an explanation on its use, the written matter includes what is called a package insert and the like, which provide an explanation relating to use, efficacy, administration method and the like.

EXAMPLES

The present invention is explained in detail in the following by referring to Examples below, which are not to be construed as limitative.

Example 1

Method

According to a conventional method, under pentobarbital anesthesia, a catheter for elemental diet administration was inserted by operation in the stomach of a male rat (body weight about 270 g), and a recovery period of one week was given. For breeding, a regular rat feed and tap water were given, and free intake was allowed. After confirmation of recovery, the rat was fasted three nights to induce lower gastrointestinal function. The fasting schedule on the day before operation, the operation day and the day after operation in the case of surgery patients was imitated.

On the day of the test, the rats were divided into 3 groups, each rat was moved to a separate observation cage, and the onset of diarrhea due to the administration of an elemental diet shown below was observed. First, one pack (80 g) of elemental diet having the composition shown in Table 1 was dissolved in water (300 cc) and prepared to show 1 kcal/cc, which was used as elemental diet 1. Three groups of an elemental diet 1 administration group as a control, an elemental diet 2 administration group, to which 1.0 w/v % (0.88 w/v % as free glutamic acid) of sodium glutamate (MSG) was added, and an elemental diet 3 administration group, to which sodium chloride (0.35 w/v %) was added, were compared. Each test elemental diet was administered using an electric pump via the catheter inserted into the stomach. The administration was started from 10:30 AM and intermittently administered 4 times per hr at 7 mL/hr. Each test elemental diet administered to one rat was 28 mL in total. The state of stool was observed from the start of the administration until 10:30 AM the next morning and, based on the severity of the symptom, ranked in 4 levels of 1. normal stool or no stool, 2. soft stool (shape was maintained), 3. muddy stool (no shape) and 4. watery stool.

TABLE 1

| component name | In 100 g (375 kcal) | In one pack (80 g) (30 kcal) | In one bottle (133 g) (500 kcal) |
|---|---|---|---|
| L-isoleucine | 803 mg | 642 mg | 1,068 mg |
| L-leucine | 1,124 mg | 899 mg | 1,495 mg |
| lysine hydrochloride | 1,110 mg | 888 mg | 1,476 mg |
| L-methionine | 810 mg | 648 mg | 1,077 mg |
| L-phenylalanine | 1,089 mg | 871 mg | 1,448 mg |
| L-threonine | 654 mg | 523 mg | 870 mg |
| L-tryptophan | 189 mg | 151 mg | 251 mg |
| L-valine | 876 mg | 701 mg | 1,165 mg |
| L-histidine hydrochloride (monohydrate) | 626 mg | 501 mg | 833 mg |
| L-arginine hydrochloride | 1,406 mg | 1,125 mg | 1,870 mg |
| L-alanine | 1,124 mg | 899 mg | 1,495 mg |
| magnesium•potassium L-aspartate | 1,295 mg | 1,036 mg | 1,722 mg |
| sodium L-aspartate (monohydrate) | 1,084 mg | 867 mg | 1,442 mg |
| L-glutamine | 2,415 mg | 1,932 mg | 3,212 mg |
| aminoacetic acid | 631 mg | 505 mg | 839 mg |
| L-proline | 788 mg | 630 mg | 1,048 mg |
| L-serine | 1,449 mg | 1,159 mg | 1,927 mg |
| L-tyrosine | 138 mg | 110 mg | 184 mg |
| dextrin | 79.26 g | 63.41 g | 105.42 g |
| sodium citrate (dihydrate) | 770 mg | 616 mg | 1,024 mg |
| potassium chloride | 188 mg | 150 mg | 250 mg |
| calcium glycerophosphate | 1,031 mg | 825 mg | 1,371 mg |
| ferrous gluconate (dihydrate) | 19.4 mg | 15.5 mg | 25.8 mg |
| zinc sulfate (heptahydrate) | 9.85 mg | 7.88 mg | 13.10 mg |
| manganous sulphate (pentahydrate) | 1.63 mg | 1.30 mg | 2.17 mg |
| copper sulfate (pentahydrate) | 1.03 mg | 0.82 mg | 1.37 mg |
| potassium iodide | 24.5 μg | 19.6 μg | 32.6 μg |
| thiamine hydrochloride | 242 μg | 194 μg | 322 μg |
| riboflavin sodium phosphate | 320 μg | 256 μg | 426 μg |
| pyridoxine hydrochloride | 334 μg | 267 μg | 444 μg |
| cyanocobalamin | 0.9 μg | 0.7 μg | 1.2 μg |
| calcium pantothenate | 1.49 mg | 1.19 mg | 1.98 mg |
| nicotinamide | 2.75 mg | 2.20 mg | 3.66 mg |
| folic acid | 55 μg | 44 μg | 73 μg |
| biotin | 49 μg | 39 μg | 65 μg |
| choline bitartrate | 22.41 mg | 17.93 mg | 29.81 mg |
| ascorbic acid | 9.75 mg | 7.80 mg | 12.97 mg |
| retinol acetate granule | 16.2 mg (810 IU) | 13.0 mg (648 IU) | 21.5 mg (1,077 IU) |
| tocopherol acetate granule | 20.63 mg (4.13 IU) | 16.50 mg (3.30 IU) | 27.44 mg (5.49 IU) |
| ergocalciferol | 1.6 μg (64 IU) | 1.3 μg (51 IU) | 2.1 μg (85 IU) |
| phytonadione | 11 μg | 9 μg | 15 μg |
| soybean oil | 636 mg | 509 mg | 846 mg |

As the additives, potassium sorbate, polysorbate 80, aspartame (L-phenylalanine compound), and a flavoring were contained.

Results

As shown in FIG. 1, rank 4 watery stool was observed in 12 cases out of 12 cases in the non-addition group. On the other hand, in the sodium glutamate addition group, rank 1 normal stool or no stool was observed in 4 cases out of 13 cases, rank 2 soft stool was observed in 1 case, and rank 3 muddy stool was observed in 2 cases. In the sodium chloride addition group, moreover, rank 1 was observed in 1 case out of 11 cases, and rank 3 was observed in 6 cases. By the detection of Kruskal-Wallis, a significant improvement effect was found in the sodium glutamate addition group (p<0.05).

Example 2

Method

A method according to Example 1 was employed. Three groups of an elemental diet 1 administration group (similar to that in Example 1) as a control, an elemental diet 4 administration group, to which 0.50 w/v % (0.44 w/v % as free glutamic acid) of sodium glutamate (MSG) was added, and an elemental diet 5 administration group, to which 0.20 w/v % (0.17 w/v % as free inosinic acid) of sodium inosinate (IMP) was added, were compared. Each test elemental diet was administered using an electric pump via the catheter inserted into the stomach. An experiment method similar to that in Example 1 was employed.

Results

Figure 2:
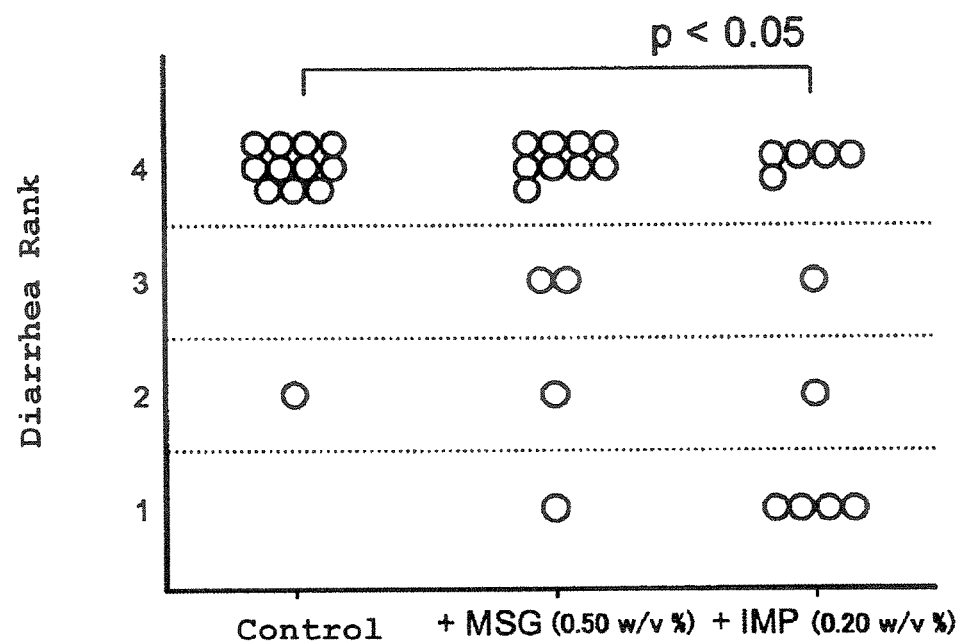
FIG. 2 shows the results of Example 2.

As shown in FIG. 2, rank 4 watery stool was observed in 11 cases out of 12 cases in the non-addition group. In the sodium glutamate addition group, rank 1 normal stool or no stool was observed in 1 case out of 13 cases, rank 2 soft stool was observed in 1 case, and rank 3 muddy stool was observed in 2 cases. In the sodium inosinate addition group, moreover, rank 1 was observed in 4 cases out of 11 cases, rank 2 was observed in 1 case and rank 3 was observed in 1 case. By the detection of Kruskal-Wallis, a significant improvement effect was found in the sodium inosinate addition group (p<0.05).

Example 3

Method

A method according to Example 1 was employed. Three groups of an elemental diet 1 administration group having the composition shown in a separate table as a control, an elemental diet 6 administration group, to which 0.04 w/v % (0.036 w/v % as free guanylic acid) of sodium guanylate (GMP) was added, and an elemental diet 7 administration group, to which 0.20 w/v % (0.18 w/v % as free guanylic acid) was added, were compared. Each test elemental diet was administered using an electric pump via the catheter inserted into the stomach. An experiment method similar to that in Example 1 was employed.

Results

Figure 3:
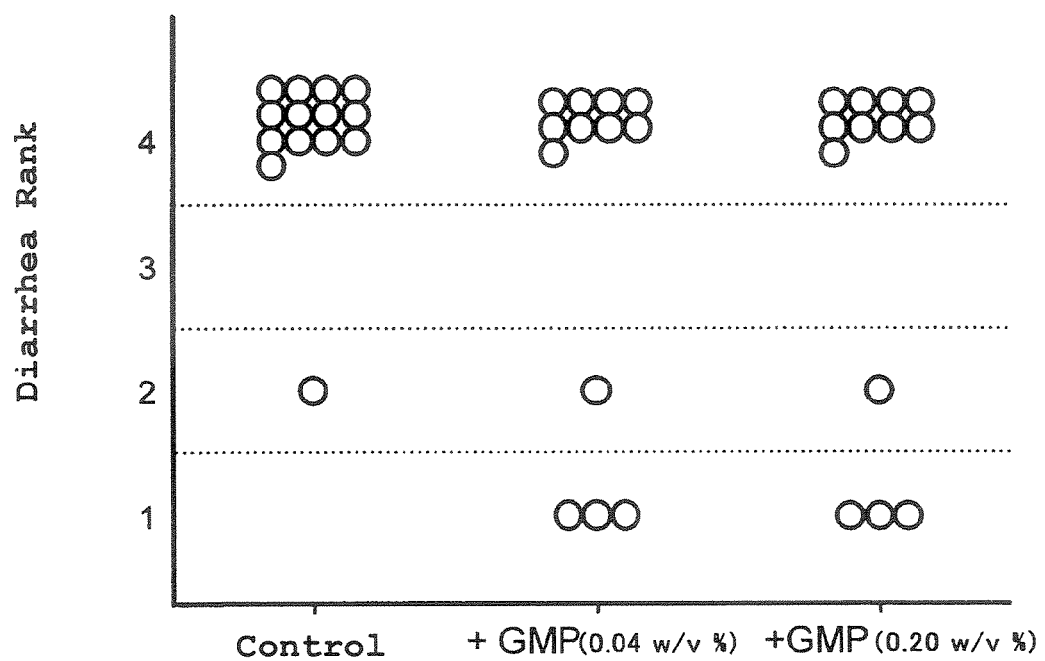
FIG. 3 shows the results of Example 3.

As shown in FIG. 3, rank 4 watery stool was observed in 13 cases out of 14 cases in the non-addition group, and rank 2 soft stool was observed in 1 case. In the sodium guanylate 0.04 w/v % addition group, rank 1 normal stool or no stool was observed in 3 cases out of 13 cases, rank 2 soft stool was observed in 1 case, and rank 4 watery stool was observed in 9 cases. In the sodium guanylate 0.20 w/v % addition group, rank 1 normal stool or no stool was observed in 3 cases out of 13 cases, rank 2 soft stool was observed in 1 case, and rank 4 watery stool was observed in 9 cases. Thus, a diarrhea symptom-improving effect was considered to be observed by the addition.

INDUSTRIAL APPLICABILITY

The present invention relates to a nutritional composition and a composition for the prophylaxis or improvement of lower gastrointestinal function, which improve lower gastrointestinal capability, markedly decrease the frequency of incidence of diarrhea upon administration of a liquid nutritional supplement and prevent or improve gastroesophageal reflux, which are conventional problems. As a result, the health management and improvement of QOL of patients can be made possible.

This application is based on application No. 2004-189515 filed in Japan, the contents of which are incorporated hereinto by reference.

The invention claimed is:

1. A method for the improvement of gastrointestinal function, which comprises administering, to a subject in need thereof, an effective amount of a composition comprising at least one kind selected from the group consisting of glutamic acid, a 5'-nucleotide, and a salt thereof, wherein, when glutamic acid or a salt thereof alone is administered, the amount thereof on administration is equal to the amount delivered by administering 400 to 3000 ml of a liquid which contains 0.0013 -1.3 w/v % of glutamic acid or salt thereof as free glutamic acid, and
    wherein said improvement of gastrointestinal function is a decrease in the frequency of diarrhea or a decrease in gastroesophageal reflux, and
    wherein said administering is to the stomach, duodenum, or jejunum of said subject via a nasal tube, a gastric fistula, or an intestinal fistula.

2. The method of claim 1, which comprises administration of said at least one kind as a liquid.

3. A method according to claim 1, wherein said 5'-nucleotide is selected from the group consisting of adenylic acid, inosinic acid, guanylic acid, cytidylic acid, uridylic acid, xanthylic acid, and a mixture thereof.

4. A method according to claim 1, wherein inosinic acid, adenylic acid, guanylic acid, cytidylic acid and uridylic acid are not administered at the same time.

5. A method according to claim 1, wherein the total amount of adenylic acid, inosinic acid, guanylic acid, cytidylic acid, uridylic acid, xanthylic acid or a salt thereof administered is equal to the amount delivered by administering 400 to 3000 ml of a liquid which contains a total amount of adenylic acid, inosinic acid, guanylic acid, cytidylic acid, uridylic acid, xanthylic acid or a salt thereof of 0.0035-0.41 w/v % as free acid.

6. A method according to claim 1, wherein said improvement of lower gastrointestinal function is a decrease in the frequency of diarrhea.

7. A method according to claim 1, wherein said improvement of lower gastrointestinal function is a decrease in gastroesophageal reflux.

8. A method according to claim 1, which comprises administration of said at least one kind prior to the administration of a liquid nutritional supplement.

9. A method according to claim 1, wherein said administering is from a gastric fistula or intestinal fistula.

10. A method according to claim 1, which comprises administering said glutamic acid or salt thereof in an amount equal to the amount delivered by administering 400 to 3000 ml of a liquid which contains 0.0013 to 1.3 w/v % of glutamic acid or salt thereof as free glutamic acid.

11. A method according to claim 1, which comprises administering said glutamic acid or salt thereof in an amount equal to the amount delivered by administering 800 to 1200 ml of a liquid which contains 0.0013 to 1.3 w/v % of glutamic acid or salt thereof as free glutamic acid.

12. A method according to claim 1, which comprises administering said glutamic acid or salt thereof in an amount equal to the amount delivered by administering 400 to 3000 ml of a liquid which contains 0.44 to 0.88 w/v% of glutamic acid or salt thereof as free glutamic acid.

13. A method according to claim 1, which comprises administering said glutamic acid or salt thereof in an amount equal to the amount delivered by administering 800 to 1200 ml of a liquid which contains 0.44 to 0.88 w/v % of glutamic acid or salt thereof as free glutamic acid.

14. A method according to claim 1, which comprises administering said 5'-nucleotide or salt thereof in an amount equal to the amount delivered by administering 400 to 3000 ml of a liquid which contains 0.0035 to 0.41 w/v % of said 5'-nucleotide or salt thereof as free acid.

15. A method according to claim 1, which comprises administering said 5'-nucleotide or salt thereof in an amount equal to the amount delivered by administering 800 to 1200 ml of a liquid which contains 0.0035 to 0.41 w/v % of said 5'-nucleotide or salt thereof as free acid.

16. A method according to claim 1, which comprises administering said 5'-nucleotide or salt thereof in an amount equal to the amount delivered by administering 400 to 3000 ml of a liquid which contains 0.035 to 0.35 w/v % of said 5'-nucleotide or salt thereof as free acid.

17. A method according to claim 1, which comprises administering said 5'-nucleotide or salt thereof in an amount equal to the amount delivered by administering 800 to 1200 ml of a liquid which contains 0.035 to 0.35 w/v % of said 5'-nucleotide or salt thereof as free acid.

* * * * *